(12) United States Patent
Isaacson et al.

(10) Patent No.: US 11,964,118 B2
(45) Date of Patent: *Apr. 23, 2024

(54) NEEDLE POSITION INDICATOR

(71) Applicant: Becton, Dickinson and Company, Franklin Lakes, NJ (US)

(72) Inventors: S. Ray Isaacson, Layton, UT (US); Paul Walker, Monkton, MD (US); Marty Stout, South Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/730,302

(22) Filed: Apr. 27, 2022

(65) Prior Publication Data

US 2022/0249809 A1 Aug. 11, 2022

Related U.S. Application Data

(63) Continuation of application No. 16/002,699, filed on Jun. 7, 2018, now Pat. No. 11,338,113.

(51) Int. Cl.
*A61M 25/06* (2006.01)
*A61B 17/34* (2006.01)
*A61B 90/00* (2016.01)
*A61M 25/00* (2006.01)

(52) U.S. Cl.
CPC ..... *A61M 25/0606* (2013.01); *A61B 17/3417* (2013.01); *A61B 2017/3454* (2013.01); *A61B 2090/0801* (2016.02); *A61B 2090/0807* (2016.02); *A61M 2025/0008* (2013.01); *A61M 2205/584* (2013.01)

(58) Field of Classification Search
CPC .......... A61M 25/0606; A61M 2205/58; A61M 2205/582; A61M 2205/583; A61B 2090/0811; A61B 2090/0812; A61B 2090/0807

See application file for complete search history.

(56) References Cited

U.S. PATENT DOCUMENTS

| | | | | |
|---|---|---|---|---|
| 5,246,426 | A * | 9/1993 | Lewis | A61M 25/0693 604/168.01 |
| 11,338,113 | B2 | 5/2022 | Isaacson et al. | |
| 2003/0204169 | A1* | 10/2003 | Howell | B29C 48/13 264/209.3 |
| 2007/0049999 | A1 | 3/2007 | Esch et al. | |
| 2007/0191775 | A1* | 8/2007 | Diep | A61M 25/0612 604/164.01 |
| 2008/0097330 | A1 | 4/2008 | King et al. | |

(Continued)

FOREIGN PATENT DOCUMENTS

| | | |
|---|---|---|
| DE | 102016112598 | 1/2018 |
| JP | 2009527286 A | 7/2009 |

(Continued)

*Primary Examiner* — Ariana Zimbouski
*Assistant Examiner* — Anna E Goldberg-Richmeier
(74) *Attorney, Agent, or Firm* — Kirton McConkie; Whitney Blair; Kevin Stinger

(57) ABSTRACT

A catheter system having one or more needle position indicators to assist an operator in withdrawing the introducer needle to a "parked" position, as part of a catheterization procedure, wherein the needle position indicator provides a visual indication to the operator.

9 Claims, 12 Drawing Sheets

(56) References Cited

U.S. PATENT DOCUMENTS

| | | |
|---|---|---|
| 2012/0232499 A1* | 9/2012 | Stout ................ A61M 25/0637 |
| | | 604/256 |
| 2012/0296275 A1 | 11/2012 | Martin |
| 2015/0223977 A1 | 4/2015 | Oberkircher et al. |
| 2016/0089180 A1 | 3/2016 | Entabi |
| 2017/0296798 A1 | 10/2017 | Kume |
| 2019/0008551 A1 | 1/2019 | Entabi |
| 2019/0388653 A1 | 12/2019 | Breindel et al. |

FOREIGN PATENT DOCUMENTS

| | | |
|---|---|---|
| WO | 2008/011258 | 1/2008 |
| WO | 2013/137348 | 9/2013 |

\* cited by examiner

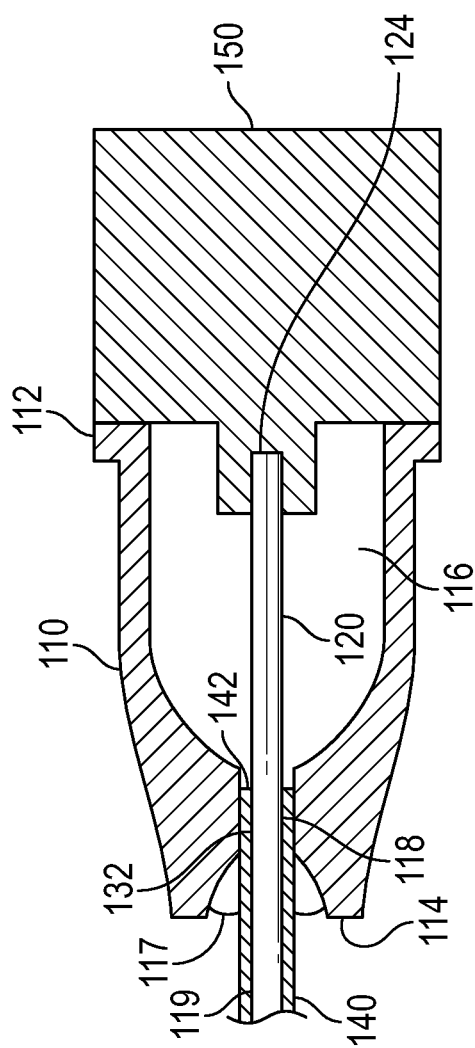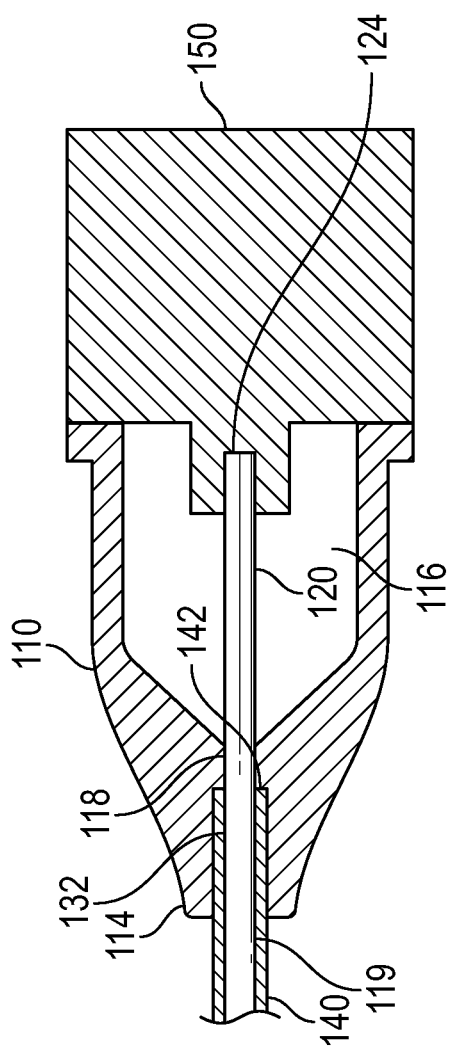

NEEDLE POSITION INDICATOR

RELATED APPLICATIONS

This application is a continuation of U.S. patent application Ser. No. 16/002,699, filed Jun. 7, 2018, and entitled NEEDLE POSITION INDICATOR which is incorporated herein in its entirety.

BACKGROUND OF THE INVENTION

Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a catheter that is inserted into a patient's vein. The catheter length may vary from a few centimeters for peripheral access to many centimeters for central access. The catheter may be inserted transcutaneously or may be surgically implanted beneath the patient's skin. The catheter may have a single lumen or multiple lumens for infusion of many fluids simultaneously.

With reference to the prior art device shown in FIGS. 1-3, conventional catheter systems generally comprise a catheter adapter 10 having a distal end 12 comprising an intravenous catheter 20 secured thereto. In some devices, the proximal end of the catheter is secured to distal end 12 and an interior portion of catheter adapter 10 via a wedge 22 that is inserted into the lumen of catheter 20, by which the proximal end of the catheter is splayed against the inner surface of catheter adapter 10 and immobilized between wedge 22 and the inner surface. In some devices, the proximal end of catheter 20 is fixedly secured to the distal end of catheter adapter 10 by an adhesive applied between the outer surface of catheter 20 and an inner or otherwise accessible surface of catheter adapter 10 that is adjacent the proximal end and/or outer surface of catheter 20. In some devices, catheter 20 is fixedly secured and/or integrated into a distal end of catheter adapter 10 through an over-molding technique, wherein the distal end of catheter adapter 10 is molded around, and thereby adhered to the proximal end of catheter 20 during the manufacturing process.

The body of the catheter adapter is generally hollow; however some catheter systems may include blood control technologies and/or safety mechanisms that may occupy this space. A proximal end 14 of the catheter adapter comprises an opening having a luer fitting for accepting secondary intravenous devices, such as intravenous tubing. The catheter system may further comprises an introducer needle 30 having a sharpened distal tip 32 that is inserted through the catheter adapter and the intravenous catheter such that the sharpened distal tip extends beyond the distal end 24 of the intravenous catheter prior to catheterization. A proximal end 34 of the introducer needle is coupled to a needle hub 40, wherein the needle hub interfaces with the proximal end of the catheter adapter prior to catheterization.

In some devices, the introducer needle 30 further comprises a notch 36 feature whereby blood flowing through the introducer needle exits the notch feature and flows into a space 16 between the outer surface of the needle and the inner surface of the intravenous catheter 20, commonly referred to as "flashback". Flashback provides a visual confirmation of successful catheterization.

In some devices, an interface 18 is provided between the outer surface of the introducer needle 30 and an interior surface of the catheter adapter 10, the intravenous catheter 20, and/or an interior surface of the wedge 22, or a similar structure of the device. Interface 18 generally comprises a surface in close proximity to the outer surface of introducer needle 30. In some devices, interface 18 comprises one or surfaces of the intravenous catheter device having in inner diameter that is approximately equal to, or minimally greater than an outer diameter of introducer needle 30, such that introducer needle 30 may bypass or translate across, or through, interface 18 without compromising the intended performance and operation of the device. In some devices, the inner diameter of interface 18 is selected to be approximately equal to, or minimally greater than an outer diameter of introducer needle 30 corresponding to the location of notch 36. As such, interface 18 minimized a gap, distance, spacing, and/or tolerance between notch 36 and respective component or surface comprising interface 18. In some devices, the dimensions of interface 18 are selected to permit passage of air between the outer surface of introducer needle 30 and the respective component or surface comprising interface 18, while simultaneously preventing passage of fluids, such as blood. Thus, fluid are permitted to flow through space 16 in proximal direction 50, but are prevented from bypassing interface 18 and flowing into the catheter adapter body or internal space of catheter adapter 10 proximal to interface 18. In some devices, the dimensions of interface 18 are selected to permit passage of air and fluids at a desired flow rate.

A common procedure of initiating the use of a conventional catheter system is as follows. A device operator will insert the distal tips of the needle and intravenous catheter, 32 and 24, respectively, into the vasculature of a patient and wait for an initial flashback of blood to confirm the catheter 20 and needle 30 are properly located within the vasculature of the patient. Once confirmed by flashback, the operator "hoods" the distal tip 32 of the needle within the intravenous catheter by withdrawing the needle in a proximal direction 50 such that the sharpened distal tip of the needle is withdrawn into the catheter proximal to the distal tip of the catheter. The operator then fully advances the catheter and needle distally 52 into the patient.

The operator then partially withdraws the needle from the catheter, temporarily "parking" the needle within the catheter at a location where the notch 36 feature is positioned in the catheter distal to the interface 18, as shown in FIG. 2. In this parked position, blood flowing through the notch feature and space 16 is contained within catheter 20 and prevented from leaking into and out of the catheter adapter body. The parked position allows the operator to gather supplies needed for making any subsequent connections. Prior to fully removing the needle from the catheter, the device operator may occlude the catheter by applying direct external pressure to the catheter, skin tissues and blood vessels, which stops blood flow through the catheter. Prior to relieving the pressure, the device operator couples the proximal end 14 of the catheter adapter to secondary intravenous device, such as a section of intravenous tubing or a plug.

The process of parking the needle requires careful attention to ensure that the needle is not overly withdrawn from the catheter. For example, if the needle is prematurely withdrawn to a point that the notch feature is positioned within the body of the catheter adapter 10, or is positioned at a location that is proximal to interface 18, as shown in FIG. 3, blood 54 will flow freely into the body of the catheter adapter, which could result in blood leakage and exposure. If the needle is prematurely withdrawn to a point where the needle entirely disengages the catheter, or the sharpened distal tip of the needle prematurely moves into the body of the catheter adapter, the device operator may further be at risk of contacting the sharpened distal tip 32.

Thus, while methods currently exist for detecting vasculature access and preventing exposure to bodily fluids during catheterization, challenges still exist. The present invention addresses and overcomes these challenges.

BRIEF SUMMARY OF THE INVENTION

The present disclosure relates generally to a needle position indicator for an intravenous catheter system, and related devices, systems, and methods. In some instances, the needle position indicator is located on or within a surface of an intravenous catheter of an intravenous catheter system. In some instances, the needle position indicator is located on an external surface of the introducer needle of an intravenous catheter system. In some instances, a catheter system is provided comprising a first needle position indicator, and a second needle position indicator selected from the group consisting of a needle position indicator located on the intravenous catheter, and a needle position indicator located on the introducer needle.

As used in the present disclosure, the term "distal" refers to a portion of the IV catheter system or component thereof that is farther from a user, and the term "proximal" refers to a portion of the IV catheter system or component thereof that is closer to the user. As used in the present disclosure, the term "operator" may refer to a clinician, doctor, nurse, or any other care provider and may include support personnel. As used herein, the term "interface" or "interface surface" refers to a surface of one or more components of a catheter system, wherein the interface is configured to eliminate and/or minimize a gap, spacing, distance, and/or tolerance between the surface and an external surface of an introducer needle of the catheter system. In some instances, an interface is provided to prevent and/or control flow of fluid within the catheter system during catheterization and prior to removal of the introducer needle from the catheter and catheter adapter of the catheter system.

In some instances, a catheter system may include one or more of the following: a catheter adapter, an intravenous catheter extending distally from the catheter adapter, an introducer needle extending through the catheter and beyond a distal tip of the catheter when the needle is in an insertion position or in an assembled configuration such that a sharpened distal tip of the needle extends beyond a distal end of the intravenous catheter, and a catheter adapter. In some instances, the catheter adapter may comprise a Luer adapter or connector that may be connectable to another vascular access device, such as blood withdrawal and/or infusion means.

In some instances, a catheter system is provided comprising a catheter adapter having a proximal end and a distal end, the distal end comprising an intravenous catheter coupled thereto, the system further comprising an introducer needle having a distal end comprising a distal opening, a proximal end, and a body extending therebetween, the distal opening being in fluid communication with an interior lumen of the introducer needle, the introducer needle further comprising an indicator provided on an outer surface of the introducer needle and having a distal end spaced from the distal opening a first distance that is greater than a second distance between a proximal end of the catheter adapter and an interface surface of the system, wherein the interface surface comprises a surface in close proximity to the outer surface of the introducer needle and configured to control fluid flow within the catheter and catheter adapter during catheterization. In some instances, the distal opening comprises a sharpened distal tip. In some instances, the distal opening comprises a notch formed through a sidewall of the introducer needle.

In some instances, the system further comprises a second indicator provided on the intravenous catheter and having a proximal end, wherein a first distance between the proximal end of the indicator and the interface or interface surface of the catheter adapter is greater than a second distance between the distal opening and a sharpened distal tip of the introducer needle. In some instances, the sharpened distal tip comprises the distal opening. In some instances, the distal opening comprises a notch formed through a sidewall of the introducer needle.

In some instances, a catheter system is provided comprising a catheter adapter having a proximal end and a distal end, the distal end comprising an intravenous catheter coupled to the catheter adapter via a wedge. In some instances, a catheter system is provided comprising a catheter adapter having a catheter coupled to a distal end of the catheter adapter via an adhesive. In some instances, a catheter system is provided comprising a catheter adapter having a catheter adhered to a distal end of the catheter adapter via an over-molding technique, wherein the distal end of the catheter adapter is molded around a proximal end of the catheter. In some instances, a catheter system of the present invention, further comprises an introducer needle having a distal end comprising a distal opening, a proximal end, and a body extending therebetween; and an indicator provided on the intravenous catheter and having a proximal end, wherein a first distance between said proximal end of the indicator and an interface or interface surface of the system is greater than a second distance between the distal opening and a sharpened distal tip of the introducer needle. In some instances, the distal opening comprises a sharpened distal tip. In some instances, the distal opening comprises a notch formed through a sidewall of the introducer needle.

In some instances, the system further comprises a second indicator on an outer surface of the introducer needle and having a distal end spaced from the distal opening a first distance that is greater than a second distance between the proximal end of the catheter adapter and the interface surface of the system.

In some instances, an introducer needle is provided comprising a sharpened distal tip, a distal opening, a proximal end, a hollow body extending between the sharpened distal tip and the proximal end, and the introducer needle further comprising an indicator provided on an outer surface of the hollow body and having a distal end spaced from the distal opening a first distance that is greater than a second distance between a proximal end of a catheter adapter and an interface surface of a catheter adapter configured to receive the introducer needle. In some instances, the interface surface is a wedge inserted into a proximal opening of the catheter to splay the proximal end of the catheter and provide an interference fit between the proximal end of the catheter and the inner surface of the distal end of the catheter adapter. In some instances, the interface surface comprises an interior surface of the intravenous catheter. In some instances, the interface surface comprises a surface of the catheter adapter, or an internal component of the catheter adapter, such as a safety device or a flow restrictor.

In various instances, an indicator of the present invention comprises at least one of a color, a line, a plurality of lines, a scale, crosshatching, an alphanumerical character, a word, a texture, a color gradient, a greyscale gradient, a shading, a progressive shading, a shape or plurality of shapes, or a combination of any of the foregoing elements. In some instances, an indicator of the present invention comprises one or more surfaces, textures, transitions or other feature configured to provide haptic feedback to the user indicating a parked or desired location of the introducer needle within the catheter, the catheter adapter, and/or an interior component of the catheter adapter.

In some instance, the present invention includes one or more methods for providing a catheter system having one or more needle position indicators. The present invention further includes one or more methods for preparing an intravenous catheter and/or an introducer needle to include a needle position indicator, wherein the method comprises locating the needle position indicator(s) in accordance with the present invention. The present invention further includes one or more methods for parking a needle during a catheterization procedure, the method including steps for utilizing a needle position indicator to withdraw the introducer needle to a parked position.

It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which:

FIG. 4B is a cross-section side view of an assembled catheter system having an intravenous catheter couple to a catheter adapter via an adhesive in accordance with a representative embodiment of the present invention;

FIG. 4C is a cross-section side view of an assembled catheter system having an intravenous catheter coupled to a catheter adapter via an over-molding process in accordance with a representative embodiment of the present invention;

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
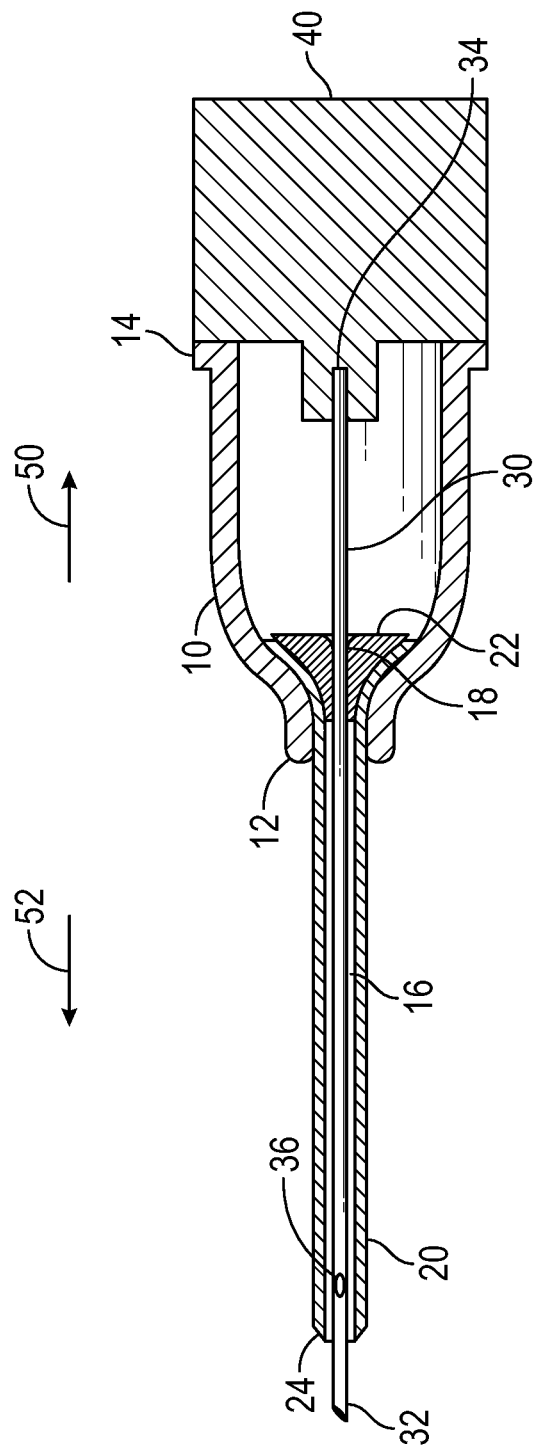
FIG. 1 is a cross-section side view of a representative PRIOR ART catheter system in an assembled configuration.
Figure 2:
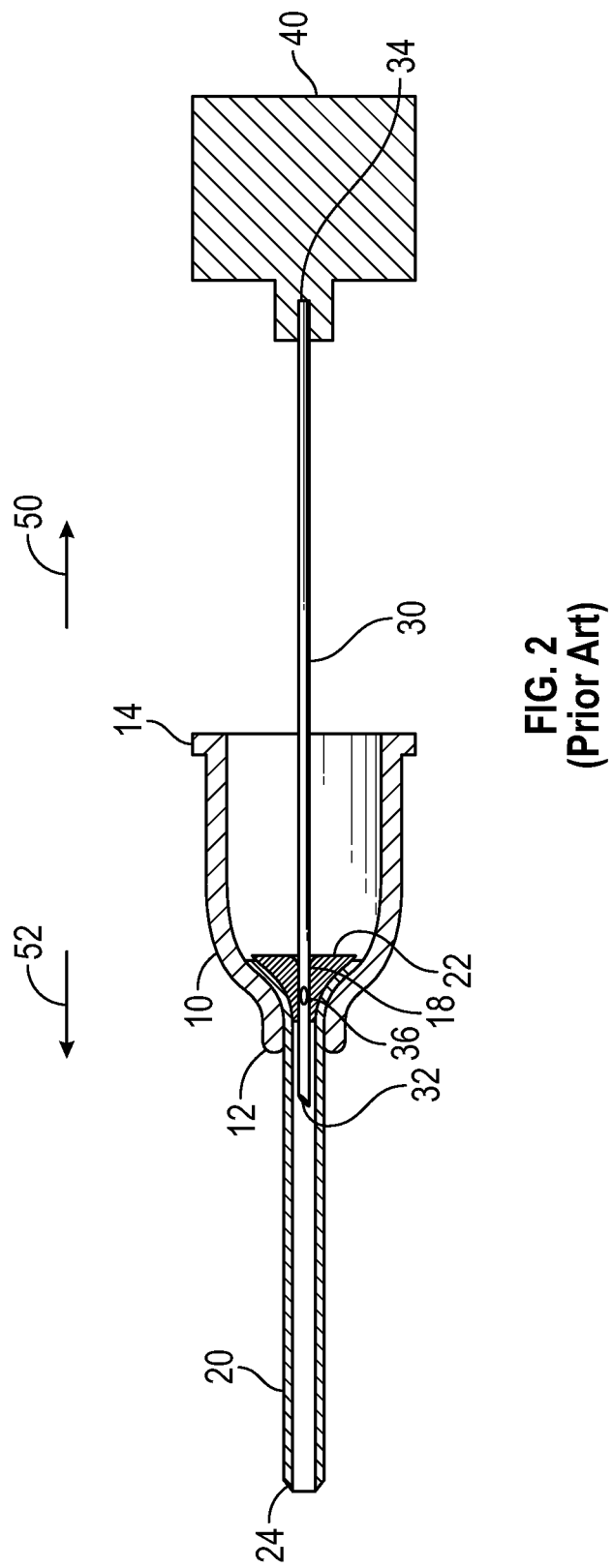
FIG. 2 is a cross-section side view of a representative PRIOR ART catheter system, wherein the introducer needle is partially withdrawn from intravenous catheter.
Figure 3:
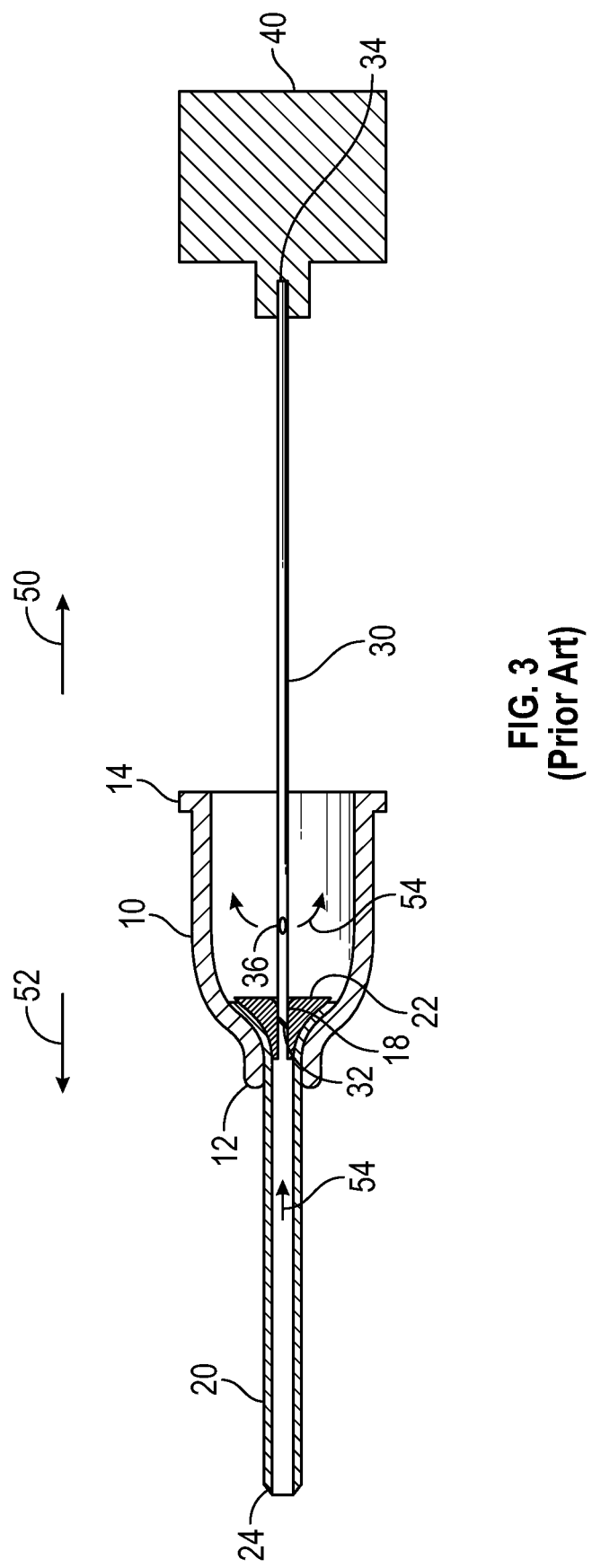
FIG. 3 is a cross-section side view of a representative PRIOR ART catheter system, wherein the introducer needle is withdrawn from the intravenous catheter to a position where a lumen of the intravenous catheter is in fluid communication with a hollow interior of the catheter adapter via a distal opening comprising a notch feature of the introducer needle.
Figure 4A:
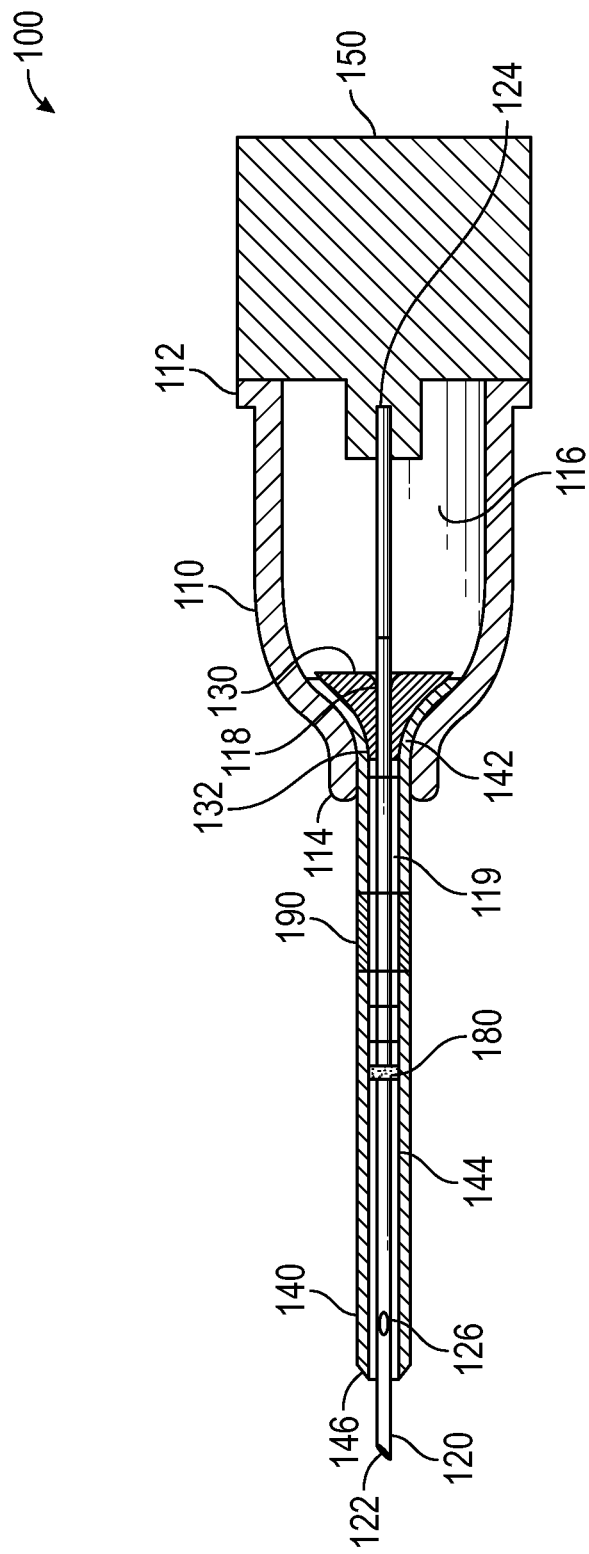
FIG. 4A is a cross-section side view of an assembled catheter system having an intravenous catheter coupled to a catheter adapter via a wedge in accordance with a representative embodiment of the present invention.

Referring now to FIG. 4A, a catheter system 100 is shown. The underlying inventive concepts of the present invention may be incorporated into any compatible catheter system. An example of a compatible catheter system 100 includes a catheter adapter 110; an introducer needle 120; an over-the-needle, peripheral intravascular catheter 140; and a needle hub 150. In some embodiments, catheter system 100 may further comprise one or more of a blood control mechanism, such as a flow control plug, a Luer access port, a passive needle-shielding mechanism, or other intravenous catheter features or elements known in the art. In some embodiments, catheter system 100 may comprise an intravenous catheter 140 coupled to a distal end of a catheter adapter 110 via a wedge 130, as shown in FIG. 4A. In some embodiments, catheter system 100 may comprise an intravenous catheter 140 coupled to a distal end of a catheter adapter 110 via an adhesive 117, as shown in FIG. 4B. In some embodiments, catheter system 100 may comprise an intravenous catheter 140 coupled to a distal end of catheter adapter 110 via an over-molding process, wherein a proximal end 142 of catheter 140 is embedded within an interior wall surface of catheter adapter 110, as shown in FIG. 4C.

With continued reference to FIGS. 4A-4C, catheter adapter 110 generally comprises a rigid or semi-rigid polymer material having a proximal end 112 comprising a Luer connector or other fitting configured to accept a secondary intravenous device, such as a syringe, an intravenous tube, a cap, or the like. Proximal end 112 further comprises an opening through which a fluid is transmitted, such as a medicament or blood. In some embodiments, catheter adapter 110 comprises a hollow interior 116. In some embodiments, interior 116 comprises one or more blood control technologies or safety features, such as a septum, a flow control plug, a needle shield, an antimicrobial coating, or the like.

Catheter adapter 110 further comprises a distal end 114 having an opening configured to receive a proximal end 142 of catheter 140. As shown in FIG. 4A, proximal end 142 is secured to distal end 114 via a wedge 130. Wedge 130 generally comprises a rigid material, such as a metal or polymer material, which is pressed into proximal end 142 and maintained in distal end 114 via a mechanical interference fit. Thus, proximal end 142 is retained between an outer surface of wedge 130 and an inner wall surface of distal end 114. Proximal end 142 may further and/or alternatively be secured to distal end 114 via an adhesive (FIG. 4B) or through an over-molding process (FIG. 4C), as is known in the art.

Catheter system 100 further comprises a central pathway 132 which provides fluid communication between the interior 116 of the catheter adapter and the lumen 144 of intravenous catheter 140. In some embodiments, central pathway 132 comprises an interface or interface surface 118. Interface 118 may comprise a surface or plurality of surfaces dimensioned and arranged to minimize a gap 119 between the outer surface of introducer needle 120 and central pathway 132. In some embodiments, interface 118 prevents and/or controls fluid flow through central pathway 132 when introducer needle 120 is positioned within central pathway 132. Thus, in some embodiments a tolerance between interface 118 and an outer surface of needle 120 prevents fluids within gap 119 from bypassing interface 118 and flowing into hollow interior 116. In some embodiments, central pathway 132 comprises a diameter that is approximately equal to an outer diameter of introducer needle 120, whereby fluids within gap 119 of catheter 140 are prevented from bypassing interface 118 when introducer needle 120 is positioned within central pathway 132. In some embodiments, interface 118 comprises an interior or lumenal surface of wedge 130, as shown in FIG. 4A. In some instances, the lumenal surface of wedge 130 comprises a distal diameter that is approximately equal to the outer diameter of introducer needle 120, and comprises a flared proximal opening, wherein interface 118 comprises a portion of the distal diameter. In some instances, interface 118 comprises a lumenal surface of catheter 140, as shown in FIG. 4B. In some instances, the lumenal surface of catheter 140 comprises a distal diameter that is approximately equal to the outer diameter of introducer needle 120, wherein interface 118 comprises a portion of the distal diameter. In some instances, interface 118 comprises an inner surface of catheter adapter 110, as shown in FIG. 4C. In some instances, the inner surface of catheter adapter 110 comprises an over-molded surface, component or feature of catheter adapter 110 in which distal end 142 is embedded during an over-molding process, wherein interface 118 comprises a lumenal portion of the over-molded surface, component or feature.

Catheter 140 generally comprises a flexible or semi-flexible polymer material that is compatible for intravenous use, for example, silicone, polyurethane, polyethylene, polyvinylchloride, PTFE and nylon. Catheter 140 may comprise any gauge and length as may be required to access a desired blood vessel. Catheter 140 comprises a distal tip 146 that may be tapered to facilitate ease of insertion during catheterization. Lumen 144 of catheter 140 generally comprises a diameter that is slightly larger than the outer diameter of introducer needle 120. As such, fluids may flow between the outer surface of needle 120 and the inner surface of catheter 140, such as during a flashback event.

Introducer needle 120 generally comprises a rigid metallic material comprising a tube having a proximal end, a distal opening, and a body extending therebetween, as is known in the art. When inserted within central pathway 132, a sharpened distal tip 122 of introducer needle 120 extends distally beyond catheter tip 146 prior to catheterization. In some embodiments, sharpened distal tip 122 comprises a distal opening. Needle 120 further comprises a proximal end 124 that is secured in a needle hub 150. Needle 120 is slidably inserted and housed within catheter adapter 110 and catheter 140 prior to catheterization. In some embodiments, a distal opening of needle 120 comprises a notch 126 feature formed through a sidewall of the needle body, wherein notch 126 provides fluid communication between the interior of needle 120 and the outer surface of needle 120, such as the Instaflash™ notch by Becton, Dickinson and Company. During catheterization, notch 126 permits blood flowing within needle 120 to flow out of needle 120 and into the lumen 144 of catheter 140, thereby providing a flashback indication.

The present invention further provides one or more needle position indicators 180 and/or 190 whereby a user or operator of the catheter system may visualize a position of the needle 120, and more specifically a position of a distal opening (i.e., notch 126 and/or sharpened distal tip 122) relative to the interface 118 and hollow interior 116 of the catheter system 100. In some embodiments, catheter system 100 comprises a single needle position indicator 180. In some embodiments, catheter system 100 comprises a single needle position indicator 190. In some embodiments, catheter system 100 comprises a first needle position indicator, and further comprises a second needle position indicator selected from the group consisting of indicator 180 and indicator 190.

In some embodiments, needle position indicator 180 comprises a marking provided on a surface of introducer needle 120. In some instances, needle position indicator 180 is provided on an exterior surface of introducer needle 120. In some embodiments, indicator 180 is formed into the material of introduce needle 120.

In some embodiments, needle position indicator 180 comprises a color that is easily seen by the operator through the clear or translucent material of intravenous catheter 140 and/or catheter adapter 110. In some embodiments, indicator 180 comprises a line or series of lines. In some embodiments, the line or series of lines represent a scale or visual measurement by which the operator is capable of determining a position of the needle within or relative to at least one of the intravenous catheter 140, the interface surface 118, and the catheter adapter 110. For example, the scale or visual measurement may be represented by varied line thicknesses and/or varied spacing between adjacent lines. In some embodiments, the scale or visual measurement may be represented through a color or greyscale gradient or by shading. In some embodiments, the line or series of lines is a crosshatching pattern. In some embodiments, indicator 180 comprises one or more alphanumerical characters. In some embodiments, indicator 180 comprises a texture or other feature that is visually perceptible to the operator. In some embodiments, indicator 180 comprises a combination of two or more of the aforementioned elements.

In some embodiments, needle position indicator 190 comprises a marking provided on a surface of intravenous catheter 140. In some instances, needle position indicator 190 is provided on an exterior or outer surface of the intravenous catheter. In some instances, needle position indicator 190 is coextruded with intravenous catheter 140, such that at least a portion of the indicator is located within a sidewall of the intravenous catheter. In some embodiments, needle position indicator 190 is provided on an interior surface of intravenous catheter 140, wherein intravenous catheter 140 is clear or translucent such that needle position indicator 190 is visible through the catheter material.

In some embodiments, needle position indicator 190 comprises a color that is easily seen by the operator. In some embodiments, indicator 190 comprises a line or a series of lines. In some embodiments, the line or series of lines represent a scale or visual measurement by which the operator is capable of determining a position of the needle within or relative to at least one of the intravenous catheter 140, the interface surface 118, and the catheter adapter 110. For example, the scale or visual measurement may be represented by varied line thicknesses and/or varied spacing between adjacent lines. In some embodiments, the scale or visual measurement may be represented through a color or greyscale gradient or by shading. In some embodiments, the line or series of lines is a crosshatching pattern. In some embodiments, indicator 190 comprises one or more alphanumerical characters. In some embodiments, indicator 190 comprises a texture or feature that is visually perceptible to the operator. In some embodiments, indicator 190 comprises a combination of two or more of the aforementioned elements.

Figure 5:
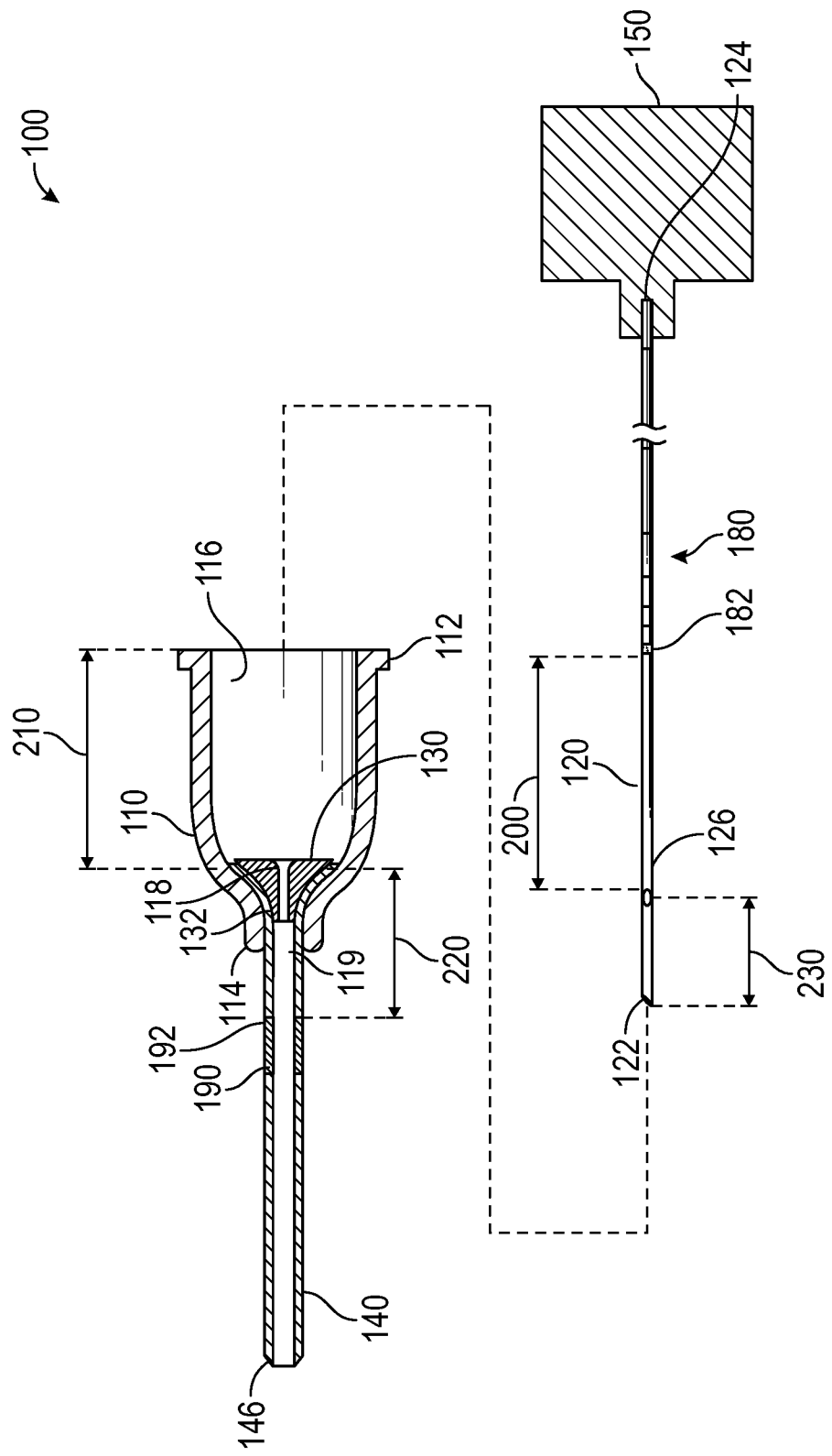
FIG. 5 is an exploded cross-section side view of a catheter system in accordance with a representative embodiment of the present invention.

Referring now to FIG. 5, an exploded, cross-sectioned view of catheter system 100 is shown. Generally, the positions of indicators 180 and/or 190 are precisely selected to provide accurate visual location of introducer needle 120 within intravenous catheter 140, and more specifically the accurate visual location of a distal opening (i.e., notch 126 and/or sharpened distal tip 122) relative to interface 118 and hollow interior 116.

In some embodiments, indicator 180 comprises a distal end 182 that is spaced from notch 126 a first distance 200 that is greater than a second distance 210 between proximal end 112 and interface surface 118 of catheter adapter 110. A length of indicator 180 may extend from distal end 182 towards proximal end 124 and may comprise any desired length. In some instances, distal end 182 comprises a pronounced or distinguished marking to indicate the distal end of the indicator to the operator.

In some embodiments, indicator 190 comprises a proximal end 192 that is spaced from interface surface 118 a first distance 220 that is greater than a second distance 230 between sharpened distal tip 122 and a distal opening (i.e., notch 126 and/or sharpened distal tip 122) of introducer needle 120. A length of indicator 190 may extend from proximal end 192 towards distal tip 146 and may comprise any desired length. In some instances, proximal end 192 comprises a pronounced or distinguished marking to indicate the proximal end of the indicator to the operator.

Figure 6:
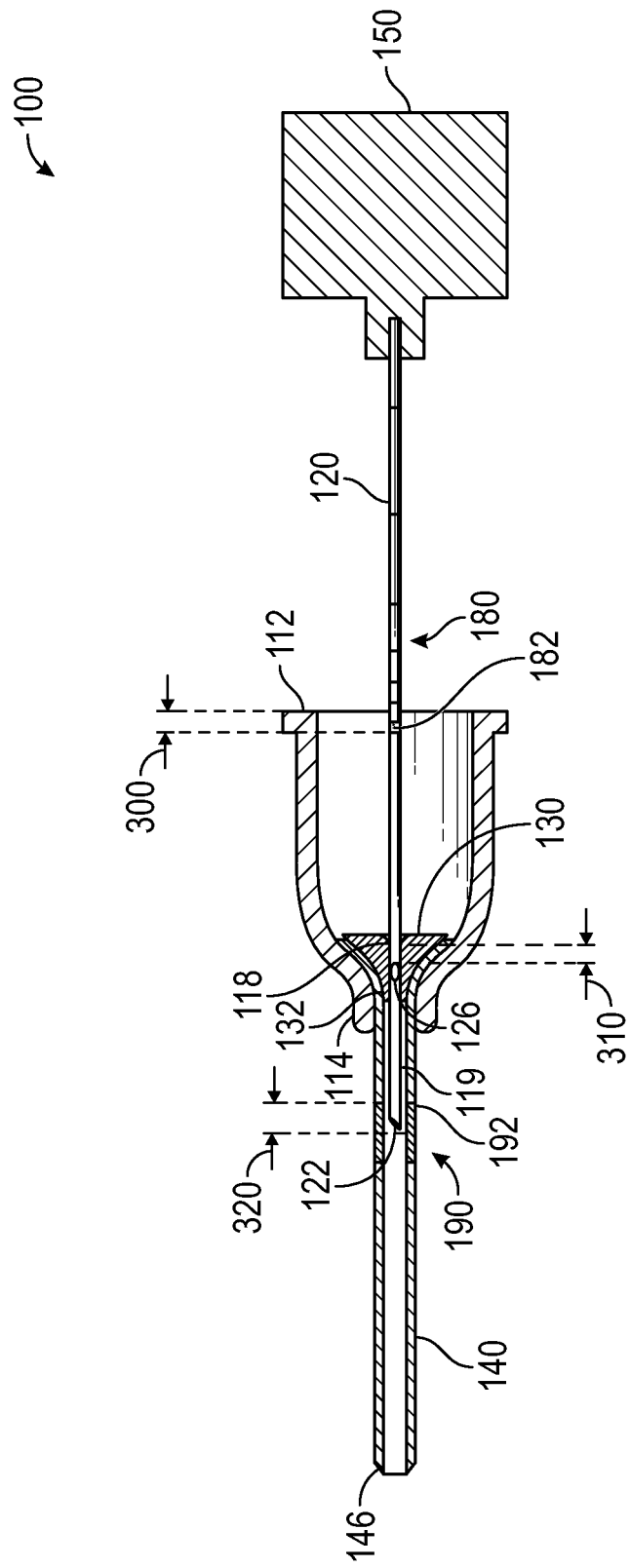
FIG. 6 is a cross-section side view of a catheter system in a parked configuration in accordance with a representative embodiment of the present invention.
Figure 7:
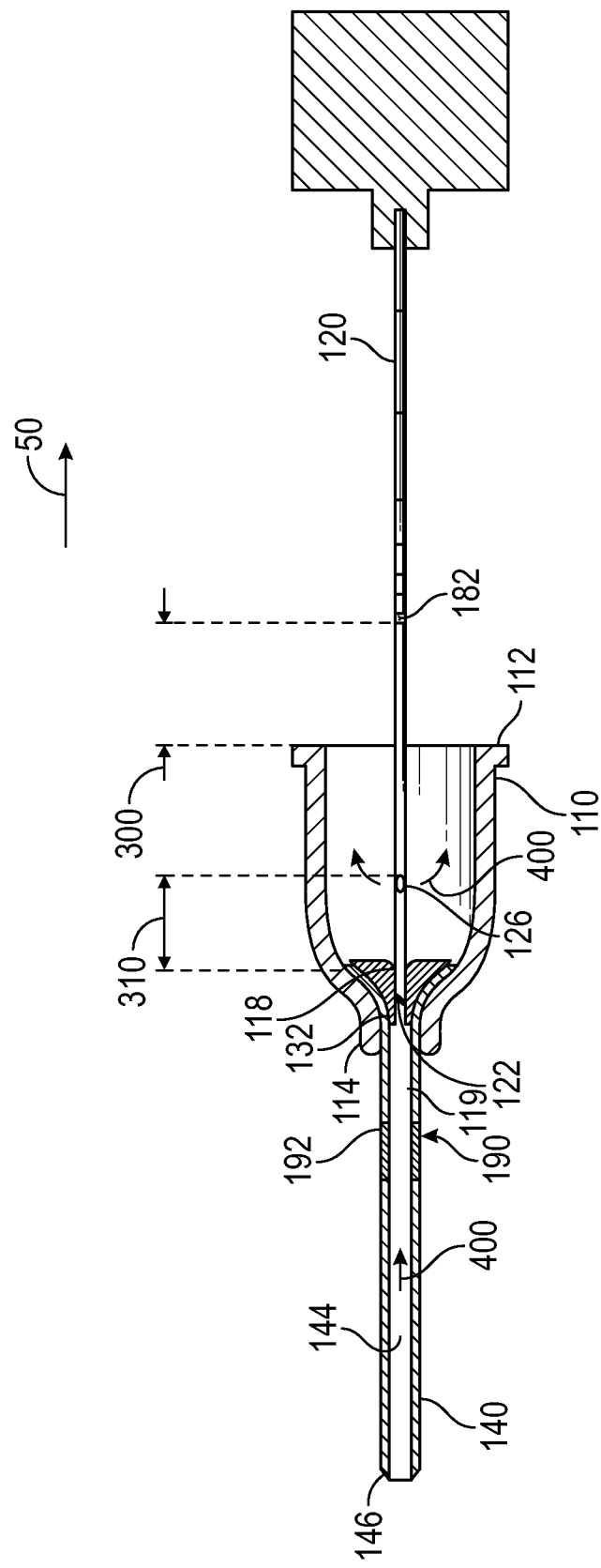
FIG. 7 is a cross-section side view of a catheter system wherein the introducer needle is withdrawn from the intravenous catheter to a position where a lumen of the intravenous catheter is in fluid communication with a hollow interior of the catheter adapter via a distal opening comprising a notch feature of the introducer needle in accordance with a representative embodiment of the present invention.

Referring now to FIGS. 6 and 7, in some embodiments a first distance 300 between distal end 182 and proximal end 112 is equal to, approximately equal to, or less than a second distance 310 between a proximal-most end or surface of interface 118 and a distal opening (i.e., notch 126 and/or sharpened distal tip 122) of introducer needle 120. Thus, an operator may visualize distal end 182 to determine a maximum withdrawal or "parking" position for introducer needle 120. In some instances, a scale of indicator 180 comprises a plurality of lines having progressively decreased spacing from a proximal end of indicator 180 to distal end 182, whereby the scale enables the operator to visually estimate and/or anticipate the location of distal end 182, which corresponds to the relative position of a distal opening of needle 120 to the proximal-most end or surface of interface 118, wherein visualization of distal end 182 represents a maximum withdrawal position, or a recommended parking position for introducer needle 120. Continued withdrawal of introducer needle 120 in proximal direction 50 will position distal end 182 proximal to proximal end 112, or external to catheter adapter 110, whereby distal opening of needle 120 is positioned within hollow interior 116 (i.e., proximal to interface 118), thereby allowing fluid communication 400 between lumen 144 of catheter 140 and hollow interior 116, as shown in FIG. 7.

With continued reference to FIGS. 6 and 7, in some embodiments a first distance 320 between proximal end 192 and sharpened distal tip 122 is equal to, approximately equal to, or less than a second distance 310. Thus, an operator may visualize and track a position of sharpened distal tip 122 relative to proximal end 192 through catheter 140 to determine a maximum withdrawal or "parking" position for introducer needle 120. In some instances, a scale of indicator 190 comprises a plurality of lines having progressively decreased spacing from a distal end of indicator 190 to proximal end 192, whereby the scale enables the operator to visually estimate and/or anticipate the location of distal opening of needle 120 relative to the proximal-most end or surface of interface 118, wherein visualization of sharpened distal tip 122 relative to proximal end 192 represents a maximum withdrawal position, or a recommended parking position for introducer needle 120.

Figure 8A:
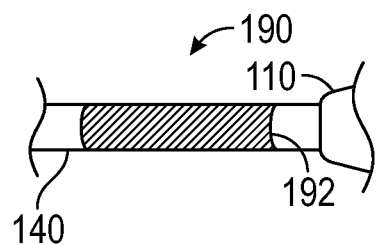
FIGS. 8A through 8E are detailed perspective views of various embodiments of a needle position indicator provided on an intravenous catheter in accordance with various representative embodiments of the present invention.
Figure 8B:
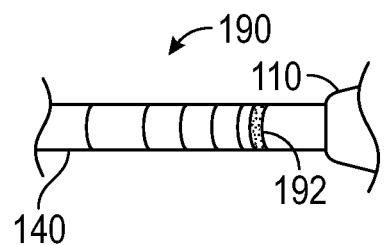
Figure 8C:
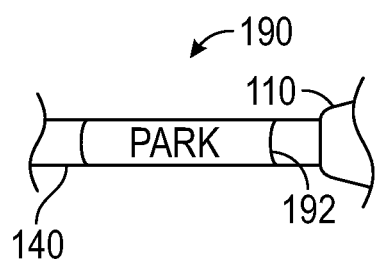
Figure 8D:
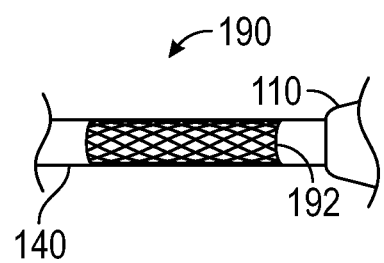
Figure 8E:
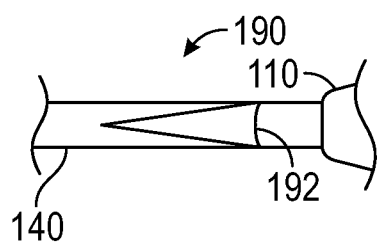

Referring now to FIGS. 8A-8E, needle position indicator 190 may comprise any size, shape, color, scale, or configuration compatible with the teaching of the present invention. For example, in some embodiments indicator 190 comprises a color, a color gradient, a greyscale gradient, a shading, and/or a progressive shading, as shown in FIG. 8A. In some embodiments, indicator 190 comprises a scale, as shown in FIG. 8B. In some instances, indicator 190 is a scale comprising a plurality of adjacent lines spaced apart from one another. In some instances, the lines are spaced apart at a constant distance. In some instance, the lines are spaced apart at progressively increasing and/or decreasing distances. In some embodiments, the lines comprise a constant line thickness. In some embodiments, the lines comprise varied line thicknesses. In some embodiment, the lines entirely circumscribe the outer diameter of catheter 140. In some embodiments, the lines partially circumscribe the outer diameter of catheter 140. In some embodiments, indicator 190 comprises one or more alphanumerical characters, for example, the word "PARK", or an equivalent word or phrase provided in a native language of the user, as shown in FIG. 8C. In some embodiments, indicator 190 comprises crosshatching, or a visually-perceptible texture, as shown in FIG. 8D. In some embodiments, indicator 190 may comprise a graphical representation, such as a shape, as shown in FIG. 8E. In some embodiments, indicator 190 comprises two or more of the aforementioned features.

Figure 9A:
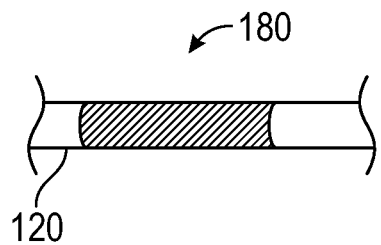
FIGS. 9A through 9E are detailed perspective views of various embodiments of a needle position indicator provided on an introducer needle in accordance with various representative embodiments of the present invention.
Figure 9B:
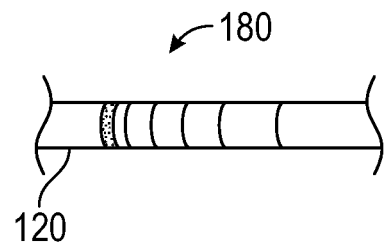
Figure 9C:
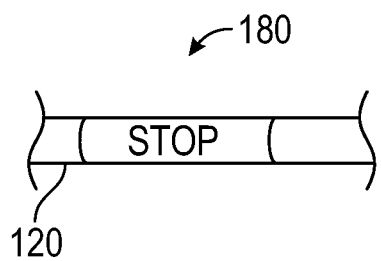
Figure 9D:
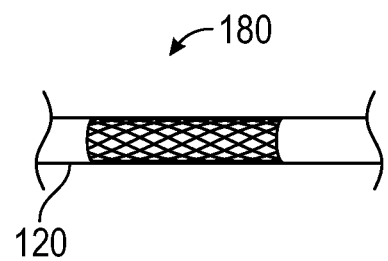

Referring now to FIGS. 9A-9E, needle position indicator 180 may comprise any size, shape, color, scale, or configuration compatible with the teaching of the present invention. For example, in some embodiments indicator 180 comprises a color, a color gradient, a greyscale gradient, a shading, and/or a progressive shading, as shown in FIG. 9A. In some embodiments, indicator 180 comprises a scale, as shown in FIG. 9B. In some instances, indicator 190 is a scale comprising a plurality of adjacent lines spaced apart from one another. In some instances, the lines are spaced apart at a constant distance. In some instance, the lines are spaced apart at progressively increasing and/or decreasing distances. In some embodiments, the lines comprise a constant line thickness. In some embodiments, the lines comprise varied line thicknesses. In some embodiment, the lines entirely circumscribe the outer diameter of needle 120. In some embodiments, the lines partially circumscribe the outer diameter of needle 120. In some embodiments, indicator 180 comprises one or more alphanumerical characters, for example, the word "STOP", or an equivalent word or phrase provided in a native language of the user, as shown in FIG. 9C. In some embodiments, indicator 180 comprises crosshatching, or a visually-perceptible, or haptically-perceptible texture or feature, as shown in FIG. 9D. For example, indicator 180 may comprise a crimp or other out-of-round feature or surface relative to the remaining outer surface of the needle or a portion of the outer surface of the needle in proximity to indicator 180. In some embodiments, indicator 180 comprises a texture of feature configured to contact interface 118 and provide a tactile feedback to the user. In some embodiments, one or more dimensions and/or surfaces comprising indicator 180 may be selected to increase, decrease, customize, or otherwise modify a tactile feedback produced through contact between indicator 180 and interface 118.

Figure 9E:
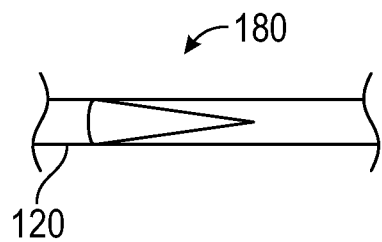

In some embodiments, indicator 180 further comprises one or more components or parts of a safety mechanism for catheter system 100. For example, in some embodiments indicator 180 comprises a crimp, ferrule or other bump-like feature configured to activate or contribute to the activation of a safety feature or mechanism of a catheter system 100. In some embodiments, indicator 180 provides at least two functions, namely, a first function comprising a tactile- or haptic-feedback to the user which indicates a "parked" position of the introducer needle 120, and a second function comprising a safety feature configured to interface with or otherwise interact with a safety mechanism of the catheter system 100. In some embodiments, indicator 180 comprises a crimp, ferrule or other bump-like feature configured to provide both a tactile-feedback or indication to the user of a position of the introducer needle 120, and a safety feature as part of a safety mechanism, wherein indicator 180 is free to move inside catheter 140 until indicator 180 contacts or approaches interface 118, or an additional haptic feature in proximity to interface 118, whereupon a tactile-feedback is provided to the user (such as a pulse, a click, a drag, an increased resistance in withdrawing needle 120, or the like), wherein the indicator 180 further contacts and/or actuates a safety mechanism simultaneous with the tactile-feedback. In some embodiments, indicator 180 activates a safety mechanism subsequent to providing a tactile-feedback. In some embodiments, indicator 180 may comprise a graphical representation, such as a shape, as shown in FIG. 9E. In some embodiments, indicator 180 comprises two or more of the aforementioned features and/or functions.

Figure 10A:
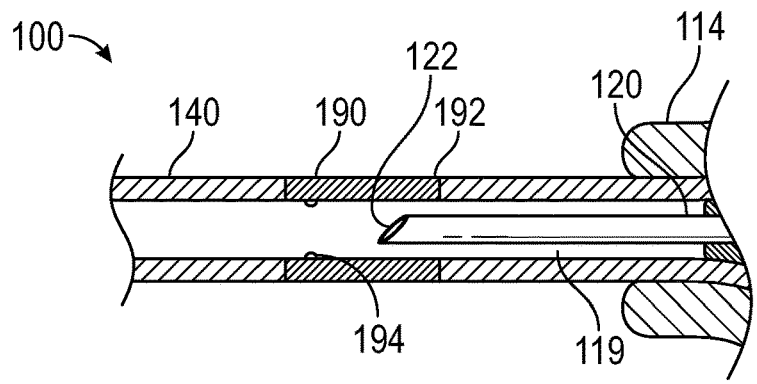
FIGS. 10A through 10C are detailed cross-section side views of a catheter system having one or more haptic features in accordance with various representative embodiments of the present invention.

In some embodiments, an indicator of the present invention further comprises one or more haptic features 194 configured to provide haptic or tactile feedback to the operator as an indication of a position of a distal opening (i.e., notch 126 and/or sharpened distal tip 122) relative to interface 118 of wedge 130. For example, in some embodiments indicator 190 comprises a haptic feature 194 that is positioned to contact a portion of introducer needle 120 and provide a haptic indication to the operator when the needle is nearing or is positioned in a desired "parked" position, as shown in FIG. 10A. Haptic feature 194 may comprise any structure, pattern, texture or feature configured to provide haptic and/or audible feedback, in accordance with the present invention. In some instances, haptic feature 194 comprises a raised inner surface, such as a bump, a ring, a channel, or other raised or recessed surface or texture. In some instances, haptic feature 194 is configured to interact with a native feature of introducer needle 120, such as the sharpened tip 122. As the sharpened tip 122 is withdrawn past haptic feature 194, pressure exerted by haptic feature 194 on the outer surface of needle 120 is released, which is perceived by the operator through touch. In some instances, the release of pressure, or the interaction between needle 120 and haptic feature 194 may produce an audible sound that is perceived by the operator. In some instances, haptic feature 194 is configured to interact with two or more surfaces of needle 120 (such as the proximal-most end of the sharpened tip 122 and the distal-most end of sharpened tip 122), wherein each interaction provides a haptic feedback to the operator. In some instances, haptic feature 194 comprises two or more independent haptic features to provide multiple haptic feedbacks to the operator.

Figure 10B:
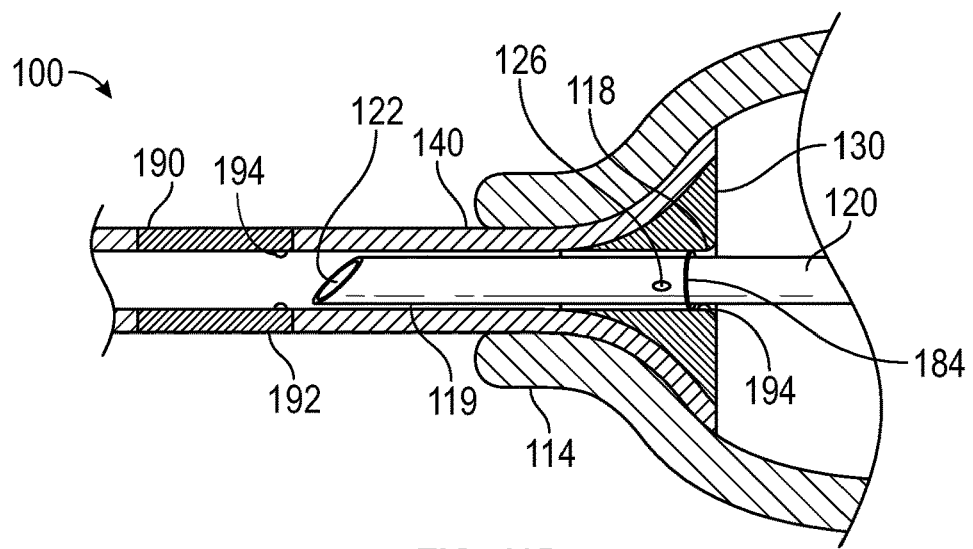

In some embodiments, introducer needle 120 further comprises a haptic feature 184 that is configured to interact with haptic feature 194 to provide a haptic feedback and/or an audible feedback to indicate a position of a distal opening (i.e., notch 126 and/or sharpened distal tip 122) relative to an interface or interface surface 118 (such as is provided by wedge 130), as shown in FIG. 10B. In some instances, haptic feature 184 comprises a raised surface of needle 120, such as a bump or a ferrule. In some embodiments, haptic feature 184 is positioned proximally to the distal opening such that the distal opening (for example, notch 126) is positioned between haptic feature 184 and sharpened tip 122. For these embodiments, haptic feature 194 may be positioned on interface surface 118, wherein an interaction between haptic features 184 and 194 indicates to the operator that the distal opening of introducer needle 140 is positioned or parked within interface surface 118.

In some embodiments, haptic feature 194 merely comprises an unmodified or unaltered surface, structure, or component of catheter system 100. For example, in some embodiments haptic feature is interface surface 118, wherein contact between haptic feature 184 and interface 118 indicates to the user a position of introducer needle 140. In some embodiments, haptic feature 194 comprises one or more surfaces or elements of a blood control device or needle safety shield device. In some embodiments, haptic feature 194 is an inner surface of catheter 140, such as a gradual or pronounced tapering of the inner diameter of catheter 140. In some embodiments, haptic feature is an inner surface of wedge 130, such as a gradual or pronounced tapering of the inner diameter of wedge 130.

In some embodiments, indicator 190 merely comprises a haptic feedback detectable to the user as a result of an interaction between the introducer needle 120 and a haptic feature 194. In some embodiments, indicator 190 merely comprises a haptic feedback detectable to the user as a result of an interaction between the introducer needle 120 and an unmodified or unaltered surface, structure, or component of catheter system 100. Thus, various embodiments and iterations of the present invention may include one or more the present indicators and haptic features to indicate to the user a position of introducer needle 140.

Figure 10C:
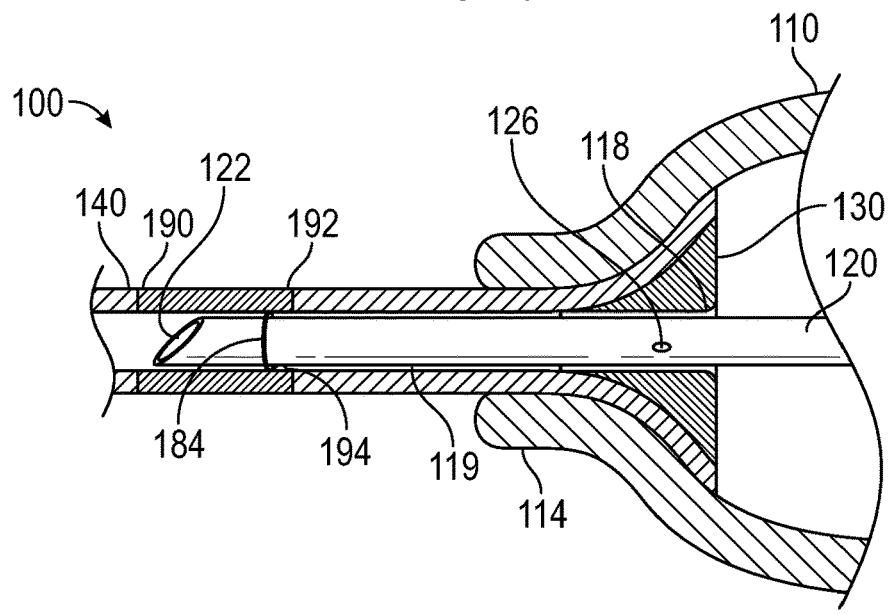

In some embodiments, haptic feature 184 is positioned distally to distal opening (i.e., notch 126) such that haptic feature 184 is positioned between the distal opening and the sharpened tip 122, as shown in FIG. 10C. For these embodiments, haptic feature 194 may be positioned within catheter 140, wherein an interaction between haptic features 184 and 194 indicates to the operator that the distal opening is positioned or parked within or distal to interface surface 118. In some embodiments, haptic feature 194 is positioned within indicator 190.

Figure 11A:
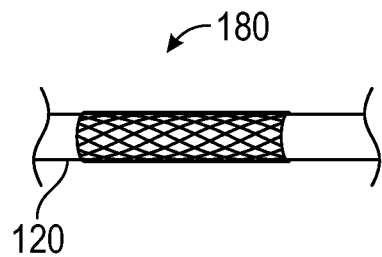
FIGS. 11A through 11E are detailed perspective views of various embodiments of a haptic feature provided on an introducer needle in accordance with various representative embodiments of the present invention.
Figure 11B:
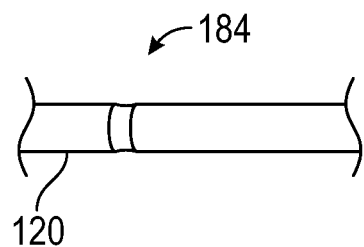
Figure 11C:
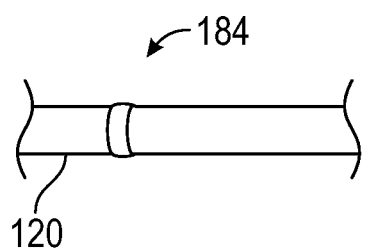
Figure 11D:
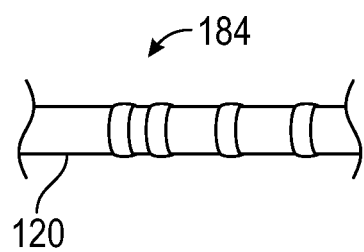
Figure 11E:
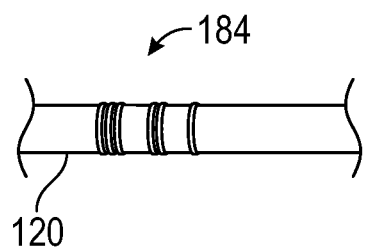

Haptic feature 184 may comprise any structure, pattern, texture or feature configured to provide haptic and/or audible feedback, in accordance with the present invention. Non-limiting examples of suitable structures, patterns, textures or features are shown in FIGS. 11A-11E. In some embodiments, haptic feature 184 comprises a raised pattern surface, such as a raised crosshatching surface, a roughened surface, or a washboard surface, as shown in FIG. 11A. Haptic feature 184 may further comprise a recessed surface, such as a groove or crimp, as shown in FIG. 11B. In some embodiments, haptic feature 184 comprises a single raised bump, such as a ferrule, a crimp, or a portion of needle 120 that is out-of round, as shown in FIG. 11C. In some embodiments, haptic feature 184 comprises a plurality of raised bumps, as shown in FIGS. 11D and 11E. In some instances, the raised bumps are evenly spaced. In some instances, the raised bumps are progressively spaced. In some instances, the raised bumps are grouped together in various numbers and combinations.

The present invention may further comprise one or more methods for providing a catheter system having one or more needle position indicators, in accordance with the foregoing. The present invention may further include one or more methods for preparing an intravenous catheter and/or an introducer needle with a needle position indicator, wherein the method comprises locating the needle position indicator(s) in accordance with the foregoing. In one embodiment, the present invention provides a method for parking a needle as part of a catheterization procedure, wherein the method comprises steps for: inserting an intravenous catheter of a catheter system into a patient; and partially withdrawing the introducer needle of the catheter system from the intravenous catheter to a parked position, wherein the parked position is determined by a) locating the sharpened distal tip of the introducer needle within the needle position indicator provided on the intravenous catheter, and/or b) referencing a portion of the needle position indicator provided on the introducer needle to a proximal end of the catheter adapter.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

We claim:

1. A catheter system, comprising:
a catheter adapter having a proximal end, a distal end, and an interior extending therebetween;
an intravenous catheter having a proximal end coupled to the catheter adapter and comprising a lumen;
a central pathway in fluid communication with the interior of the catheter adapter and the lumen of the intravenous catheter;
a wedge disposed within the catheter adapter and securing the intravenous catheter within the catheter adapter, wherein the wedge comprises an interface surface;
an introducer needle positioned within the central pathway and comprising a sharpened distal tip, a proximal end, a body extending therebetween, and a notch formed through a side wall of the body and in fluid communication with an interior lumen of the introducer needle;
a haptic feature within the intravenous catheter, wherein when the sharpened distal tip is withdrawn past the haptic feature, pressure exerted by the haptic feature on an outer surface of the introducer needle is released, wherein when the sharp distal tip is withdrawn past the haptic feature and the notch is within the wedge, pressure exerted by the haptic feature on an outer surface of the introducer needle is released; and
an indicator provided on the intravenous catheter and having a distal end and a proximal end, wherein when the sharpened distal tip is between the distal end of the indicator and the proximal end of the indicator, the notch is disposed distal to a proximal-most end of the interface surface and proximal to a distal end of the interface surface.

2. The catheter system of claim 1, wherein the wedge comprises an wherein the central pathway extends through the interface surface, wherein blood is prevented from flowing out of the notch when the notch is within the wedge at the interface surface.

3. The catheter system of claim 1, wherein the haptic feature is between the proximal end and the distal end of the indicator.

4. The catheter system of claim 1, wherein the haptic feature comprises a raised inner surface.

5. The catheter system of claim 1, wherein the introducer needle comprises another haptic feature configured to interact with the haptic feature.

6. The catheter system of claim 5, wherein the another haptic feature comprises a raised surface.

7. A catheter system, comprising:
a catheter adapter having a proximal end, a distal end, and an interior extending therebetween;
an intravenous catheter having a proximal end coupled to the catheter adapter and comprising a lumen;
a central pathway in fluid communication with the interior of the catheter adapter and the lumen of the intravenous catheter;
a wedge disposed within the catheter adapter and securing the intravenous catheter within the catheter adapter, wherein the wedge comprises an interface surface, wherein the central pathway extends through the interface surface, wherein blood is prevented from flowing out of a notch when the notch is within the wedge at the interface surface;

an introducer needle positioned within the central pathway and comprising a sharpened distal tip, a proximal end, a body extending therebetween, the notch formed through a side wall of the body and in fluid communication with an interior lumen of the introducer needle, and a haptic feature; and an indicator provided on the intravenous catheter; and another haptic feature between a distal end of the indicator and a proximal end of the indicator or between a distal end of the interface surface and a proximal end of the interface surface, wherein the other haptic feature is configured to interact with the haptic feature when the notch is between the proximal end of the interface surface and the distal end of the interface surface.

8. The catheter system of claim 7, wherein the other haptic feature comprises a raised surface.

9. The catheter system of claim 7, wherein the haptic feature comprises a raised surface.

\* \* \* \* \*